United States Patent

Reynaud et al.

[11] Patent Number: 6,012,924
[45] Date of Patent: Jan. 11, 2000

[54] PROSTHETIC ELEMENT, PARTICULARLY A TOOTH POST MADE OF COMPOSITE MATERIAL

[75] Inventors: Marc Reynaud, 23, avenue de la Plaine Fleurie, 38240 Meylan; Pierre-Luc Reynaud, 9, rue du Rif Tronchard, 38120 Saint Egneve; Mahn Chu, Saint-Egreve, all of France

[73] Assignees: Marc Reynaud, Meylan, France; Pierre-Luc Reynaud, Saint-Egreve, France

[21] Appl. No.: 08/836,765

[22] PCT Filed: Nov. 21, 1995

[86] PCT No.: PCT/FR95/01532

§ 371 Date: Dec. 15, 1997

§ 102(e) Date: Dec. 15, 1997

[87] PCT Pub. No.: WO96/15759

PCT Pub. Date: May 30, 1996

[30] Foreign Application Priority Data

Nov. 21, 1994 [FR] France .................... 94/13910

[51] Int. Cl.⁷ .......................... A61K 6/087; A61K 6/027; A61L 27/00
[52] U.S. Cl. ........................................ 433/220; 433/228.1
[58] Field of Search .................... 433/220, 224, 433/226, 228.1

[56] References Cited

U.S. PATENT DOCUMENTS

| | | |
|---|---|---|
| 3,493,403 | 2/1970 | Tung et al. . |
| 3,911,581 | 10/1975 | Dietz ................................. 433/228.1 |
| 4,121,940 | 10/1978 | Michel et al. .......................... 433/224 |
| 4,350,532 | 9/1982 | Randklev ............................ 433/228.1 |
| 4,503,169 | 3/1985 | Randklev ............................ 433/228.1 |
| 4,894,012 | 1/1990 | Goldberg et al. ...................... 433/215 |
| 5,088,927 | 2/1992 | Lee ........................................ 433/224 |
| 5,328,372 | 7/1994 | Reynaud et al. ........................ 433/220 |
| 5,518,399 | 5/1996 | Sicurelli, Jr. et al. ................. 433/220 |

FOREIGN PATENT DOCUMENTS

| | | |
|---|---|---|
| 0 432 001 | 6/1991 | European Pat. Off. . |
| 0 462 512 | 12/1991 | European Pat. Off. . |
| 2 641 697 | 7/1990 | France . |
| 2 669 211 | 5/1992 | France ................................. 433/220 |
| 94 00 070 | 5/1994 | Germany . |
| 2 028 855 | 3/1980 | United Kingdom . |
| 2 064 550 | 6/1981 | United Kingdom ................ 433/228.1 |
| WO 89/04640 | 6/1989 | WIPO . |

*Primary Examiner*—Ralph A. Lewis
*Attorney, Agent, or Firm*—Young & Thompson

[57] ABSTRACT

A shaped member made of composite material for making a prosthetic element, particularly a tooth post, comprising a core of longitudinal fibers embedded in a resin matrix, and a method for making the member, are disclosed. The member is characterized in that the resin matrix contains at least one metal oxide.

19 Claims, 1 Drawing Sheet

PROSTHETIC ELEMENT, PARTICULARLY A TOOTH POST MADE OF COMPOSITE MATERIAL

FIELD OF THE INVENTION

The present invention relates to a section of composite material intended to constitute a prosthetic element, and particularly a tooth post, as well as to a process for manufacturing such a section.

BACKGROUND OF THE INVENTION

It is known that, in the dental domain, in order to ensure the perennity of the dental substance of a tooth, metal posts are called upon, which are screwed or sealed therein. Such metal posts present a certain number of drawbacks, which are principally associated with the great difference which exists between the mechanical characteristics of these posts and those of the dentine in which they are disposed.

In order to avoid such drawbacks, it has been proposed to employ posts made of composite material, constituted in particular by a matrix of bio-compatible resin, and particularly an epoxy resin, in which carbon or glass fibers are embedded.

In certain embodiments, the fibers are longitudinal fibers which extend over the whole length of the post and which are under equal tension therein. The posts thus constituted, by reason of their mechanical characteristics close to those of the dentine, considerably reduce the drawbacks set forth hereinabove.

However, such posts present the drawback of being transparent to X-rays, so that their positioning is particularly difficult to establish with the aid of the conventional apparatus available to practitioners.

These posts are usually manufactured by pultrusion, i.e. by a process of extrusion in which both the fibers, particularly the carbon or glass fibers, and a resin matrix are passed in the same die at the same time, the fibers being, all along the operation, maintained under tension. This operation of pultrusion is sometimes difficult to carry out by reason of the problems of obturation of the die of the extruder which occur during operation.

In the prior state of the art, products, or charges, are known, which are added to the dental reconstitution pastes, in order to give them a certain opacity to X-rays. U.S. Pat. No. 4,503,169 thus proposes to that end to include zirconium, oxides in dental reconstitution pastes.

Patent GB-A-2 028 855 also discloses a settable composition exempt of mercury based on a carboxylic polyacid and which contains, inter alia, filling elements which may possibly comprise fibrous elements which may be coated with metal oxides capable of reacting with the carboxylic polyacid in order to promote bond with the matrix.

SUMMARY OF THE INVENTION

The present invention has for its object to propose a means for solving both the problems associated with carrying out the pultrusion operation and those connected with the lack of opacity of the prosthetic elements used in the dental art, which are constituted by composite materials based on resins, particularly epoxy resins, reinforced by fibers, particularly long, unidirectional carbon fibers.

The present invention thus has for an object a section of composite material intended to constitute a prosthetic element, particularly a dental post, comprising a core, constituted by longitudinal fibers, which is embedded in a matrix of resin, characterized in that this resin matrix contains at least one metal oxide.

Applicants have in fact observed that the implementation of pultrusion was largely facilitated when metal oxides were added to the resin matrix. In fact, the added metal oxide behaves like a sliding agent which reduces the adhesion of the resin and promotes flow of the product in the die of the extruder. Implementation is even easier when the metal oxides are in the form of granules or microballs. It is also possible, in order to facilitate the pultrusion operation further, to use metal oxides which are contained in microballs, particularly glass microballs.

Under these conditions, the metal oxides introduced in the resin perform two functions, namely a first function of slide provoking the extrusion and a second function of opacity.

As set forth hereinafter, when one is obliged to add a relatively large quantity of metal oxides in the resin, oxides contained in glass microballs are totally or partly employed. A plurality of particles of oxides may, moreover, be grouped in the same microball.

According to the invention, the metal oxide or oxides chosen, necessary for giving the desired opacity to the prosthetic element, may be associated, wholly or partly, with the fibers, i.e. it is either introduced therein or disposed on their surface so as to constitute a coating adhering well thereto. In this last embodiment, the cohesion of the fibers with the resin is thus improved.

In an embodiment of the invention, the metal oxide presents a refraction index higher than the refraction index of the dentine. Such an embodiment of the invention is particularly interesting in that, with identical resultant overall opacity, the quantity of said metal oxide contained in the resin can be reduced, which avoids diminishing the mechanical qualities of the post. In addition, it is thus possible, for a given desired refraction index, to control the quantity of metal oxide used, in order to place in the post only the quantity which allows the sliding agent to act in optimum manner, which promotes the pultrusion operation.

The present invention also has for an object a process for manufacturing a section of composite material, intended to constitute a prosthetic element, and particularly a dental post, comprising a core constituted by longitudinal fibers, this core being embedded in a matrix of resin, characterized in that it comprises the steps consisting in mixing with said resin matrix at least one metal oxide, and in extruding the fibers and the resin matrix containing said metal oxide, while maintaining said fibers under equal tension.

In an embodiment of the invention, the metal oxides may be associated with the fibers, i.e. be introduced in the mass thereof or on their surface.

At least one of the metal oxides associated with the fibers may be identical to that, or to one of them, mixed with the resin matrix. Furthermore, the refraction index of the oxide used may advantageously be greater than the refraction index of the dentine.

In a particularly interesting embodiment of the invention, the fibers coated with metal oxides receive a specific bridging agent intended to promote bonding thereof with the resin matrix, this bridging agent being constituted, in the majority of cases, by silanes.

The coating of metal oxide may be made on the whole surface of the fibers, particularly by a thermic impregnation, when the melting temperature of the fibers is higher than that of the metal oxides. Under such conditions, the granulometry of the metal oxides has only little influence on the radio-opacity. The coating may also be made, particularly in the case of the melting temperature of the fibers being lower than that of the metal oxide, by employing a process of projection, and in particular a plasma projection process.

According to this embodiment, the fibers coming from storage reels traverse an impregnation tank where they are impregnated with metal oxide in the molten state, then these fibers are drained and dried in a second enclosure of which the temperature progressively decreases.

BRIEF DESCRIPTION OF THE DRAWINGS

A form of embodiment of the present invention will be described hereinafter by way of non-limiting example, with reference to the accompanying drawing, in which.

DETAILED DESCRIPTION OF THE INVENTION

According to the invention, dental posts are constituted by incorporating in a matrix constituted by a thermosettable resin, or a thermoplastic resin, metal oxides which are biocompatible, in order not to provoke problems of acceptation by the patient's organism. The quantity of metal oxide introduced in the resin is a function of the refraction index which it is desired to obtain. These oxides preferably present a refraction index higher than that of the dentine, and even than that of the osseous structure, and preferably much greater than them.

It is known that the refraction index of the osseous structure is of the order of 1.65 and that that of the dentine is of the order of 1.6. Under these conditions, for the dental prosthetic element to be detectable by X-rays, it must present a refraction index different from that of the dentine and/or the osseous structure, viz. it is slightly higher or lower than them. The refraction indices of the dental post must thus be either higher than 1.65 or lower than 1.6 if it is desired to be able to distinguish them both from the dentine or from the osseous structure.

The most interesting metal oxides which may thus be capable of being used in the implementation of the present invention are:

| | |
|---|---|
| magnesium oxide MgO | n = 1.74 |
| strontium oxide SrO | n = 1.81 |
| calcium oxide $CaO_2$ | n = 1.89 |
| bariumoxide BaO | n = 1.98 |
| $BaO_2$ | n = 1.98 |
| zinc oxide ZnO | n = 2.01 to 2.03 |

-continued

| | |
|---|---|
| zirconium oxide $ZrO_2$ | n = 2.13 to 2.20 |
| titanium oxide $TiO_2$ | n = 2.61 to 2.90 |

The quantity of metal oxide introduced in the resin depends on the refraction index which it is desired to give the post.

Figure 1:
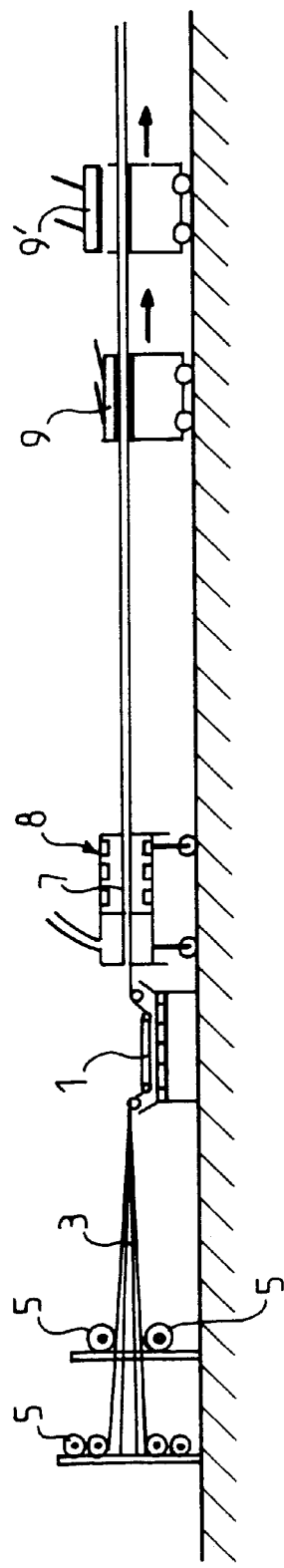
FIG. 1 is a schematic view illustrating a general embodiment of sections according to the invention.

In a first step of the process according to the invention, the metal oxide chosen is firstly blended with a resin matrix, for example by mixing. In a second step, as shown in FIG. 1, a bundle of fibers 3, particularly carbon or glass fibers, which are stored on reels 5, are passed in a tank 1 containing the mixture of resin and chosen metal oxides. The assembly traverses a die 7 of an extruder 8 and, simultaneously to this extrusion, the fibers 3 are subjected to a tension by a system of drawing constituted in known manner by "caterpillars" 9, 9'. On leaving the die 7, the composite section obtained is polymerized. If such a section is intended to constitute dental posts, it is then cut to the desired length and possibly machined.

In a first example of embodiment of the invention, a mixture of epoxy resin with 25% by weight of barium oxide and 25% by weight of titanium oxide is made. Physically, the metal oxides introduced in the resin matrix are in the form of granules whose mean granulometry is less than the mean diameter of the fibers. The fibers used are high performance carbon fibers with a diameter of the order of 8 μm, which are preferably grouped together in tufts of 3000 to 6000 filaments. The diameter of the die 7 is such that a section with a diameter of about 2 mm is obtained on leaving the extruder 8. Such a section is particularly adapted to be used for making dental posts.

The radio-opacity of the section obtained has proved greater than that of the dentine, its refraction index being 1.69. If such a section is used as dental post, it is perfectly locatable in X-ray examinations when the tooth is observed towards the root.

In a second example of embodiment of the invention, a mixture of epoxy resin with 39% by weight of titanium oxide is made. Physically, the titanium fixed with the resin is, as before, in the form of microballs whose mean granulometry is of the order of 2 μm. The fibers used are high performance carbon fibers with a diameter of the order of 8 μm. The diameter of the die used is the same as previously.

Upon examination, the radio-opacity of the section obtained has proved to be much greater, not only than that of the dentine, but also than that of the osseous structure, and that of the enamel of the tooth (n=1.65), its refraction index being 1.82, so that such a section is locatable by X-rays even through the enamel of a tooth.

As mentioned hereinabove, it was observed, during the different implementations of the invention, that the passage of the product (i.e. of the assembly constituted on the one hand, by the mixture of resin and metal oxides and, on the other hand, the fibers) in the die of the extruder was rendered more difficult when the sections were of small diameter and necessitated large quantities of metal oxides in order to attain the desired refraction index.

In order to avoid this drawback, the fibers themselves are coated with a given metal oxide or with a mixture of several metal oxides. In such an embodiment, the fibers may possibly receive a prior treatment intended to promote catching thereof with the metal oxides with which it is desired to coat them. After such a coating, the fibers may be stored in a reel while awaiting their subsequent use. Such a modus operandi makes it possible, for a determined quantity of metal oxides necessary for ensuring the desired opacity, to reduce that mixed with the resin matrix, which diminishes the compactness of the resin/metal oxide mixture and at the same time improves the passage of the product in the die.

It is thus possible to obtain sections of composite material incorporating carbon fibers under equal tension which present high refraction indices, much higher than those of the adjacent osseous structure, which presents considerable interest in numerous medical applications such as for example articular implants, etc.

In order to coat the fibers with the metal oxides, they are preferably passed in a bath containing the molten metal oxides. When the melting temperature of a given oxide is higher than that of the fiber, which is particularly the case when it is desired to coat glass fibers with titanium oxide, a process of plasma projection of the metal oxide may be employed.

In a third example of embodiment of the invention, the proportions of titanium oxide and of barium oxide given in the first example are taken, but the barium oxide is deposited on the fibers and the titanium oxide is mixed with the resin. In this way, the fibers may be coated by hot immersion as the high value of the melting temperature of the titanium oxide is no hindrance, since the latter is mixed with the resin. It is thus possible, in this case, to use not only carbon fibers but also glass fibers since the melting temperature of the barium oxide is less than that of the glass.

According to the invention, the same metal oxide as that deposited on the fibers may be mixed with the resin matrix.

More than two metal oxides may of course be mixed with the resin. A fourth example of embodiment of the invention will be described hereinafter in which 8.5% by weight of zirconium oxide, 10.5% by weight of titanium oxide and 17.5% by weight of barium oxide are mixed with an epoxy resin.

The titanium and barium metal oxides are, in the present embodiment of the invention, introduced in the form of microballs. These oxides are both included in the same glass microball with a granulometry of the order of 20 to 40 $\mu$m. Zirconium oxide is in the form of granulates whose granulometry is of the order of a micrometer. The fibers used are high performance carbon fibers with a diameter of the order of 8 $\mu$m. The diameter of the die is such that a section with a diameter of 2 mm is obtained at the outlet of the extruder.

Upon examination, the radio-opacity of the section obtained proved to be slightly greater than that of the dentine, since its refraction index is 1.66. A simple dental radiograph of a section inserted in a tooth confirmed a radio-opacity of this section slightly greater than that of the dentine.

The metal oxides disposed in microballs proved to be particularly efficient sliding agents, which makes it possible to introduce them in large quantities in the resin without provoking packing at the level of the die of the extruder. For a given desired refraction index, their use makes it possible to control the quantity of metal oxide used, in order to place in the post only the quantity which allows the sliding agent to act in optimum manner, which promotes the pultrusion operation.

In order to improve adherence of the fibers, or the fibers coated with oxides, with the resin matrix, they may be sized prior to being introduced in the resin. Such sizing consists, in known manner, in making a surface treatment of the fibers, coated or not, with the aid of a "binding" agent whose role is to constitute a chemical bridging with the molecules of the resin matrix.

Figure 2:
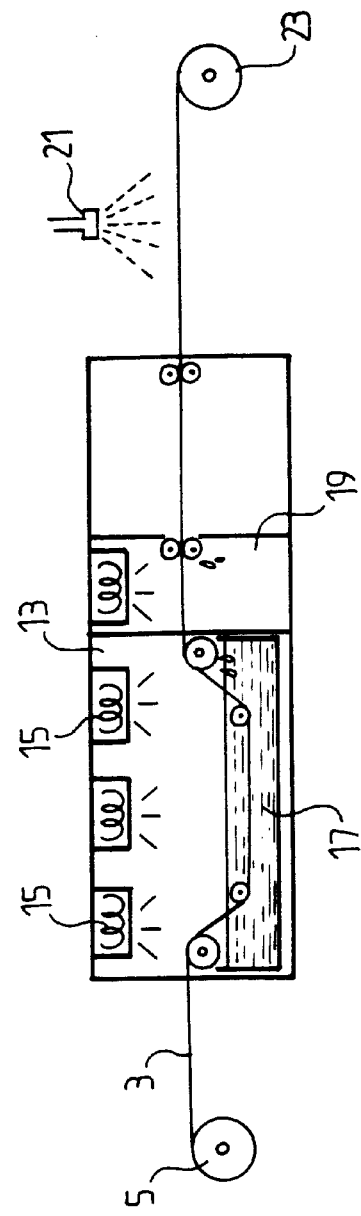
FIG. 2 is a schematic view of a variant embodiment of the invention.

To that end, as shown in FIG. 2, fibers 3 stored on reels 5 are admitted in an enclosure 13 heated by resistors 15, where the metal oxides 17 are maintained in the molten state, then in a draining and drying enclosure 19 where the temperature decreases progressively. At the outlet of the enclosure 19, spray means 21 project onto the fibers the binding element chosen, and finally the treated fibers are wound on a storage reel 23.

The metal oxides may also be incorporated in the fiber itself. For example, particularly in the case of glass fibers, the metal oxides may be introduced in the fibers during manufacture thereof.

The metal oxides may, in the same section, be both in the form of granules or microballs, and in a heterogeneous form. The majority will preferably be in the form of microballs.

What is claimed is:

1. A shaped member made of composite material intended to constitute a prosthetic element, comprising a core constituted by longitudinal fibers, said core being embedded in a matrix of resin which contains at least one metal oxide in an amount effective to provoke a sliding effect during extrusion, said metal oxide being in the form of granules or microballs having dimensions which are smaller than the mean diameter of the fibers.

2. The shaped member according to claim 1, wherein the metal oxide is associated with the fibers.

3. The shaped member according to claim 2, wherein the metal oxide associated with the fibers is disposed on the surface of the fibers.

4. The shaped member according to claim 2, wherein the fibers are glass fibers, and the metal oxide associated with the fibers is incorporated within the fibers.

5. The shaped member according to claim 2, wherein the metal oxide associated with the fibers is common with that or one of those contained in the resin matrix.

6. The shaped member according to claim 1, wherein the metal oxide presents a refraction index higher than the refraction index of dentine.

7. The shaped member according to claim 1, wherein the metal oxide is contained in a glass microball.

8. The shaped member according to claim 1, wherein the fibers are coated with a bridging agent intended to connect said fibers to the resin matrix.

9. The shaped member according to claim 1, wherein the metal oxide is selected form the group consisting of MgO, SrO, $CaO_2$, BaO, $BaO_2$, ZnO, $ZrO_2$, $TiO_2$, and mixtures thereof.

10. Process for manufacturing a shaped member of composite material intended to constitute a prosthetic element and having a core constituted by longitudinal fibers, said core being embedded in a matrix of resin, the process comprising:

mixing an effective amount of at least one metal oxide with said resin matrix to provoke a sliding effect during extrusion, said metal oxide being in the form of granules or microballs having dimensions which are smaller than the mean diameter of the fibers; and extruding the fibers and the resin matrix containing said metal oxide.

11. Process according to claim 10, further comprising associating with the fibers at least one metal oxide having a refraction index which is higher than the refraction index of dentine.

12. Process according to claim 11, wherein the metal oxide associated with the fibers is coated on the surface of the fibers.

13. Process according to claim 12, wherein the metal oxide is coated over the whole surface of the fibers by passing the fibers in a bath containing at least one molten metal oxide.

14. Process according to claim 12, wherein the metal oxide coating is made by a process of plasma projection.

15. Process according to claim 11, wherein the fibers are associated with the metal oxide by passing the fibers through an impregnation tank containing at least one metal oxide in the molten state, then draining the fibers, and drying them in an enclosure whose temperature decreases progressively.

16. Process according to claim 11, wherein after having been associated with the metal oxide, the fibers are coated with a specific bridging agent intended to connect them to the resin matrix.

17. Process according to claim 16, wherein the bridging agent is a silane.

18. Process according to claim 10, wherein the fibers are glass fibers and the metal oxide associated with the fibers is incorporated within the fibers during manufacture thereof.

19. Process according to claim 10, wherein at least one of the metal oxides associated with the fibers is identical to that, or one of those, mixed with the resin matrix.

* * * * *